US011077036B2

(12) United States Patent
Price et al.

(10) Patent No.: US 11,077,036 B2
(45) Date of Patent: Aug. 3, 2021

(54) LACTAM SOLUBILITY

(71) Applicant: Conopco, Inc., Englewood Cliffs, NJ (US)

(72) Inventors: Paul Damien Price, Wirral (GB); Neil James Parry, Tarporley (GB)

(73) Assignee: Conopco, Inc., Englewood Cliffs, NJ (US)

(*) Notice: Subject to any disclaimer, the term of this patent is extended or adjusted under 35 U.S.C. 154(b) by 423 days.

(21) Appl. No.: 15/750,901

(22) PCT Filed: Jul. 28, 2016

(86) PCT No.: PCT/EP2016/068008
§ 371 (c)(1),
(2) Date: Feb. 7, 2018

(87) PCT Pub. No.: WO2017/029092
PCT Pub. Date: Feb. 23, 2017

(65) Prior Publication Data
US 2020/0085711 A1 Mar. 19, 2020

(30) Foreign Application Priority Data
Aug. 20, 2015 (EP) .................... 15181856

(51) Int. Cl.
*A61K 8/37* (2006.01)
*A61K 8/49* (2006.01)
*A61Q 17/00* (2006.01)
*A61Q 19/00* (2006.01)

(52) U.S. Cl.
CPC .............. *A61K 8/37* (2013.01); *A61K 8/4913* (2013.01); *A61Q 17/005* (2013.01); *A61Q 19/00* (2013.01)

(58) Field of Classification Search
CPC ............................ A61K 38/00; C11D 3/3776
USPC ....................................................... 424/404
See application file for complete search history.

(56) References Cited

U.S. PATENT DOCUMENTS

| | | | |
|---|---|---|---|
| 5,955,419 | A | 9/1999 | Barket, Jr. et al. |
| 7,985,722 | B2 | 7/2011 | DeSanto |
| 8,641,948 | B2 | 2/2014 | Ghogh et al. |
| 9,586,901 | B2 | 3/2017 | Kumar et al. |
| 9,930,888 | B2 | 4/2018 | Parry et al. |
| 10,306,886 | B2 | 6/2019 | Price |
| 2007/0269473 | A1 | 11/2007 | Nelson |
| 2009/0175810 | A1* | 7/2009 | Winckle ............... A61K 9/0014 424/61 |
| 2011/0059144 | A1 | 3/2011 | Fletcher et al. |
| 2011/0257115 | A1 | 10/2011 | Leighton |
| 2012/0190667 | A1 | 7/2012 | Ghogh et al. |
| 2013/0142855 | A1 | 6/2013 | Gross et al. |
| 2013/0190377 | A1 | 7/2013 | Kumar et al. |
| 2013/0330292 | A1 | 12/2013 | Lei et al. |
| 2014/0017287 | A1 | 1/2014 | Lei et al. |
| 2014/0296336 | A1 | 10/2014 | Berndl et al. |
| 2015/0073069 | A1* | 3/2015 | De Gans ................ C08K 5/544 523/435 |

FOREIGN PATENT DOCUMENTS

| | | |
|---|---|---|
| CN | 1169112 | 12/1997 |
| CN | 1688543 | 10/2005 |
| CN | 101410372 | 4/2009 |
| CN | 101932300 | 12/2010 |
| CN | 102257117 | 11/2011 |
| CN | 103260609 | 8/2013 |
| WO | WO2004016588 | 2/2004 |
| WO | WO2006085089 | 8/2006 |
| WO | WO2007008504 | 1/2007 |
| WO | WO2007085042 | 8/2007 |
| WO | WO2010069742 | 6/2010 |
| WO | WO2012156250 | 11/2012 |
| WO | WO2014118240 | 8/2014 |
| WO | WO 2017029112 | 2/2017 |

OTHER PUBLICATIONS

Chirravuri et al. Functions of hydrotropes in solutions, 2011 (Year: 2011).*
Carla S.M. Pereira et al., Ethyl lactate as a solvent: properties, applications and production processes—a review, Green Chemistry, 2011, pp. 2658-2671; XP055235519, vol. 13, No. 10.
IPRP in PCTEP2016069072, Aug. 2, 2017.
IPRP2 in PCTEP2016068585, Nov. 2, 2017.
IPRP2 in PCTEP2016068625, Sep. 6, 2017.
Mary E. Davey et al., Rhamnolipid Surfactant production Affects Biofilm Architecture in Pseudomonas aeruginosa PAO1, Journal of Bacteriology, 2003, pp. 1027-1036, vol. 185, No. 3, American Society for Microbiology.
Ondrej Krenk et al., Methodology for Synthesis of Enantiopure 3,5-Disubstituted Pyrrol-2-ones, European Journal of Organic Chemistry, 2015, pp. 5414-5423; XP002752111.
Search Report & Written Opinion in EP15181849, dated Feb. 23, 2016.
Search Report & Written Opinion in PCTEP2016069072, dated Sep. 14, 2016.
Search Report and Written Opinion in PCTEP2016067613, dated Sep. 21, 2016.
Search Report and Written Opinion in PCTEP2016067616, dated Sep. 12, 2016.
Search Report and Written Opinion in PCTEP2016068008, dated Sep. 12, 2016.
Search Report and Written Opinion in PCTEP2016068010, dated Sep. 12, 2016.
Search Report and Written Opinion in PCTEP2016068287, dated Oct. 26, 2016.
Search Report and Written Opinion in PCTEP2016068585, dated Oct. 4, 2016.
Search Report and Written Opinion in PCTEP2016068625, dated Sep. 9, 2016.

(Continued)

*Primary Examiner* — Melissa L Fisher
(74) *Attorney, Agent, or Firm* — Foley & Lardner LLP

(57) ABSTRACT

Compositions comprising a lactam and an alkyl lactate. The compositions are suitable for use as anti-microbial, anti-biofilm and bacteriostatic compositions.

12 Claims, No Drawings

(56) References Cited

OTHER PUBLICATIONS

Search Report in EP15181842, dated Dec. 10, 2015.
Search Report in EP15181846, dated Dec. 11, 2015.
Search Report in EP15181847, dated Dec. 17, 2015.
Search Report in EP15181851, dated Dec. 11, 2015.
Search Report in EP15181856, dated Dec. 14, 2015.
Search Report in EP15181858, dated Dec. 11, 2015.
Von R. Scheffold Und P. Dubs, Synthese von Azaprotoanemoninen, Helvetica Chimica Acta, 1967, pp. 798-808; XP55249911.
Written Opinin in EP15181856, dated Dec. 14, 2015.
Written Opinion 2 in PCTEP2016067613, dated Jul. 11, 2017.
Written Opinion in EP15181842, dated Dec. 10, 2015.
Written Opinion in EP15181846, dated Dec. 11, 2015.
Written Opinion in EP15181847, dated Dec. 17, 2015.
Written Opinion in EP15181851, dated Dec. 11, 2015.
Written Opinion in EP15181858, dated Dec. 11, 2015.
Wei et al.; Measurement and Correlation of the Solubility of Penicillin V Potassium in Ethanol + Water and 1-Butyl Alcohol + Water Systems; Journal of Chemical and Engineering Data; 2015; 112-117; vol. 60, No. 1.
Lin Hui, et al.; Micellization properties of different rhamnolipidic fractions and their solubilization; Acta Scientiae Circumstantiae; 2011; 2609-2615 (with Engl. Abstract and human translation of pp. 2610 & 2614 only); 31, No. 12.
Kloeppel; Temperature inside collapsing bubble four times that of sun; News Bureau—Research, ; 2005; pp. 1-3.
Paulusse, et al.; Journal of Polymer Science: Part A: Polymer Chemistry, vol. 44, 5445-5453 (2006).
https://news.illinois.edu/view/6367/207368. Ultrasonication can induce polymer scission, polymerization, and block co-polymer formation; downloaded Jun. 8, 2020.
Mohd, et al. Ultrasonic Modification of Micelle Structures, Handbook of Ultrasonics and Sonochemistry. Springer, Singapore, Abstract; downloaded Jun. 8, 2020.
Borate et al.; Novel hybrids of fluconazole and furanones: Design, synthesis and antifungal activity; Bioorganic & Medicinal Chemistry Letters; 2011; pp. 4873-4878; vol. 21.
Munoz, et al.; Enzymatic enantiomeric resolution of phenylethylamines; Org. Biomol. Chem.; 2011; pp. 8171-8177 (abstract only—total 5 pages); vol. 9.
Luo Mingsheng, Gao Tianhu; Overview of Pharmaceutical Excipients; Overview of Pharmaceutical Excipients; 2006; pp. 627-628 (translation of relevant portions only).
Li Dongguan; technical manual of practical cosmetics production; .; 2001; pp. 43-44 (with Engl abstract and original).
Yi Weiping, Editor; Fine Chemical Products and Technology; .; 2009; pp. 33 (English abstract only—no original available).

* cited by examiner

LACTAM SOLUBILITY

This application is a U.S. National Phase Application under 35 U.S.C. § 371 of International Application No. PCT/EP2016/068008, filed on Jul. 28, 2016, which claims priority to European patent application No. 15181856.4 filed on Aug. 20, 2015, the contents of which are incorporated herein in their entireties.

The present invention relates to compositions comprising lactams and an alkyl or alkenyl lactate. The compositions are suitable for use as anti-microbial, anti-biofilm and bacteriostatic compositions.

WO 2007/085042 and WO 2004/016588 disclose lactams for antimicrobial benefit and steps towards their synthesis. WO2014/118240 discloses antimicrobial compositions comprising a lactam and a hydrotope.

However, use of these lactams is limited by relatively low solubility, especially in aqueous or substantially aqueous compositions.

The present invention relates to combinations of lactams and an alkyl or alkenyl lactate. The combination has been shown to improve lactam solubility. This is especially marked in aqueous or substantially aqueous compositions.

More specifically, the present invention relates to lactams as described in WO 2007/085042 and WO 2004/016588 in combination with an alkyl or alkenyl lactate. The contents of WO 2007/085042 and WO 2004/016588, and in particular the lactam structures explicitly drawn out therein, are incorporated by reference.

For example, in a first aspect, the present invention relates to a composition comprising a lactam and an alkyl or alkenyl lactate, wherein the lactam is a lactam of formula (I) or (II):

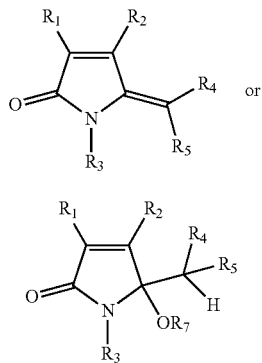

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl and —C(O)CR$_6$=CH2;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and —C(O)CR$_6$=CH$_2$; and Preferably, at least one of $R_4$ and $R_5$ is hydrogen.

It will be appreciated that, where appropriate groups may be optionally substituted. Optional substituents may include halogens, $C_{1-4}$alkyl, $C_{1-4}$haloalkyl (for example, $CF_3$) and $C_{1-4}$alkoxy.

Alkyls may, for example, be $C_{1-12}$alkyls, such as $C_{1-6}$alkyls. Aryls may, for example, be $C_{6-10}$aryls, for example, phenyls.

Preferably, at least one of $R_1$ and $R_2$ is selected from heterocyclyl, heteroaryl, aryl and arylalkyl.

Preferably, $R_1$ is hydrogen. Preferably, $R_3$ is hydrogen. Preferably, $R_4$ is hydrogen. Preferably, $R_5$ is hydrogen. Preferably, $R_6$ is hydrogen. Preferably, $R_7$ is hydrogen. Preferably, $R_2$ is aryl or aralalkyl. More preferably, $R_2$ is a phenyl group or a substituted phenyl group, for example, a mono-substituted phenyl group. Substitution may be ortho, meta, or para. Preferably, it is para. Preferred substituents include halogen and methyl. For example, and without limitation, $R_2$ may be selected from phenyl, 4-fluorophenyl, 4-chlorophenyl, 4-bromophenyl and 4-methylphenyl.

Accordingly, in a first aspect, the present invention may provide to a composition comprising a lactam and an alkyl or alkenyl lactate, wherein the lactam is a lactam of Formula Ia or Formula IIa:

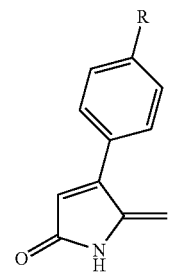

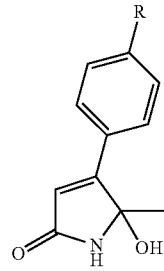

wherein R is H, halogen (preferably, F, Cl, or Br), or $C_{1-4}$alkyl (preferably methyl).

In some embodiments, the lactam is a lactam of formula Ia. In some embodiments, the lactam is a lactam of formula IIa.

Preferred lactams may include:

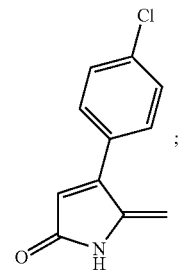

4-(4-chlorophenyl)-5-methylene-pyrrol-2-one (Ref. 488);

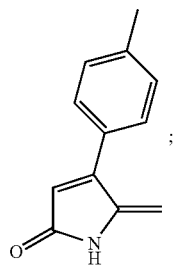

5-methylene-4-(p-tolyl)pyrrol-2-one (Ref. 491)

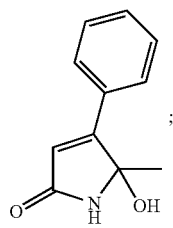

4-phenyl-5-hydroxy-5-methyl-1H-pyrrol-2-one (Ref. 131)

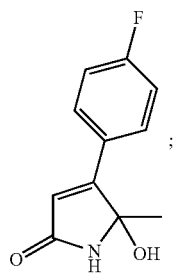

4-(4-fluorophenyl)-5-hydroxy-5-methyl-1H-pyrrol-2-one (Ref. 258)

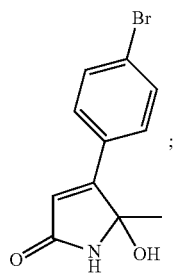

4-(4-bromophenyl)-5-hydroxy-5-methyl-1H-pyrrol-2-one (Ref. 316).

The composition may be aqueous or non-aqueous.

Preferably, the composition is aqueous or substantially aqueous. For example, the composition may be at least 40 wt % water, at least 50 wt % water, at least 60 wt % water, at least 70 wt % water.

As used herein, a distinction is made between aqueous and substantially aqueous. It will be understand that substantially aqueous composition may not be entirely aqueous in nature. For example, they may be biphasic, or contain an emulsion of a non-aqueous material in an aqueous solution.

Preferably, the composition is aqueous.

The composition may be, without limitation, any of a personal care composition, a homecare composition, a pharmaceutical composition, or an industrial composition such as an anti-biofilm coating or paint, for example, for use in maritime environments. The composition may also be an agricultural chemical. The compositions may be suitable for use as antimicrobial, anti-biofilm and bacteriostatic compositions. Non-limiting examples of such compositions are provided herein. The compositions may also be used as additive compositions; in other words, the composition may be combined with further ingredients such as excipients to form a composition as described above.

Preferably, the composition is an aqueous household care composition or an aqueous personal care composition (for example, a skin cleansing composition).

Suitably, the alkyl or alkenyl lactate is a $C_{2-20}$ alkyl or alkenyl lactate, for example a $C_{2-15}$ alkyl or alkenyl lactate. For example, the alkyl or alkenyl lactate may be a $C_{2-15}$ alkyl lactate. Alkyl and alkenyl chains may include those derived from fatty acids including palmitoleic acid, oleic acid, lauric acid, myristic acid, palmitic acid, and stearic acid. In some cases, the composition comprises an alkyl lactate as described.

Alkyl and alkenyl, as used herein, refers to both straight and branched groups. In some cases, the group is straight. In some cases, the group is branched. Where a range of carbon atoms is given for chain length, it will be appreciated that a mixture of chain lengths may be present, although in some cases, alkyl or alkenyl lactate refers to a single compound having a defined alkyl or alkenyl group.

The amount of lactate may be at least 0.01% wt. of the composition, for example, at least 0.1% wt. of the composition, at least 0.5% wt. of the composition, at least 1% wt. of the composition, or higher.

A preferred alkyl lactate is ethyl lactate. This improves solubility even at low concentrations and is classified as a "green solvent". It is environmentally benign and the raw materials for its production can be generated from biomass by fermentation.

In aqueous compositions, the amount of ethyl lactate may be up to 10% wt. of the composition. For example, it may be up to 7% wt., up to 5% wt., up to 3% wt., or even as low as up to 1% wt.

In non-aqueous compositions, the amount of ethyl lactate may be higher, for example up to 50% wt., such as up 25% wt. Naturally, the lower amounts applicable for aqueous compositions may also be used.

The alkyl or alkenyl lactate may also be a longer chain lactate. For example, the lactate may be a $C_{12-15}$ alkyl or alkenyl lactate, for example, as used in Dow Sunspheres®. It will be understood that the amounts described above may similarly apply.

Preferably the composition contains 0.000001 to 50% wt. lactam, more preferably 0.001 to 50% wt. even more preferably 0.01 to 5% wt., most preferably 0.01 to 2%.

It will be appreciated that options and preferences described with respect to the first aspect apply equally where possible to the other aspects, and vice versa.

DESCRIPTION

Lactams may be obtained using methods as described in WO 2007/085042 and WO 2004/016588, which are herein incorporated by reference in their entirety.

Compositions

The compositions described herein may be compositions having anti-microbial activity. In some cases, the compositions are anti-bacterial. They may have bactericidal and/or bacteriostatic activity. The inventor(s) have observed desirable bacteriostatic activity. Accordingly, in some cases, the composition is a bacteriostatic composition.

The compositions may also prevent and/or inhibit biofilm formation. Biofilms are formed when microorganisms stick to a surface. Biofilm extracellular polymeric substances may be formed. Biofilms (also referred to as slime) present problems in industrial environments; for example, they may form in pipes in apparatus, or industrial and agricultural structures, on solar panels, and on boat hulls and other marine structures. Biofilms may also pose a problem in domestic environments. For example, biofilms may form in domestic appliances such as washing machines. Biofilms are also present in personal care, for example, they may form on tooth surfaces.

Compositions suitable for any and all of these applications are within the scope of the invention. In some cases, the composition is a paint or other coating. In such cases, the composition may further comprise a binder, optionally a pigment and optionally one or more conventional additives (for example, to modify surface tension, improve flow properties, improve the finished appearance, increase wet edge, improve pigment stability, etc—such additives are known in the art). The composition may comprise an aqueous solvent or an organic solvent to suit purpose.

The composition may also be used in medical applications, for example to coat equipment including medical devices.

In some cases, the composition is a pharmaceutical composition. In other words, the composition may comprise a lactam as described herein and a pharmaceutically acceptable excipient. The composition may be suitable for topical use (for example, it may be a cream or lotion), it may be suitable for ocular use (for example, it may be an used as a pharmaceutical eye drop), it may be suitable for otic use (for example, it may be used as an ear drop), it may be suitable as a mouth wash, or it may be suitable for oral administration.

In some cases, the composition is a composition suitable for use in the home (often referred to as a homecare composition) or institutions. Homecare compositions include, without limitation, cleaning products, laundry detergents, and fabric conditioners. In some cases, the composition is a homecare composition, for example a laundry liquid. The composition may therefore comprise a detergent surfactant and a builder. The composition may be a fabric conditioner (also called a fabric softener) and may comprise an antistatic agent. The composition may also be a domestic cleaning product.

In some cases, the composition is a personal care composition. For example, the composition may be intended for use on the skin (for example, a cream, cleanser or serum). For example, the composition may be useful in the prevention or treatment of acne. For example, the composition may comprise one or more of dimethicone, petrolatum, a humectant such as hyaluronic acid or glycerin; and ceramide(s). In some cases, the composition is a personal care composition comprising a detergent, for example, the composition may be a face wash or shower gel or hair shampoo. The composition may be a hair treatment composition other than a shampoo. The composition may be a deodorant composition (for example, a deodorant powder, paste or liquid). The composition may be an oral care composition (such as a toothpaste or mouthwash and may include, for example, fluoride and/or flavourings).

In some cases, the composition is a contact lens cleaning fluid.

The composition may be a composition suitable for use in agriculture, for example, as a soil additive (solid or liquid).

The composition may be a composition suitable for use in the treatment of or manufacture of glass or lens for example as an additive/treatment for solar panels.

EXAMPLES

The following example uses, without limitation, 4-(4-chlorophenyl)-5-methylene-pyrrol-2-one and ethyl lactate.

Excess solid lactam (~3 mg) was placed in a Whatman® Mini Uniprep sample vial, fitted with a 0.45 µm nylon filter. Water or water+ethyl lactate (500 µL) was added the mixture shaken and tapped briefly to initially disperse the solid and the mixture then agitated for 48 hours using a plate shaker fitted with a vial holder (see image below). After 48 hours, the solid was removed from the system by pressing down the plunger with integral filter on the vial (see image below). This removes the solid and provides filtered solution within the inner chamber which is then ready for analysis.

The level of lactam dissolved in solution was quantified using HPLC analysis. Samples were analysed on an Agilent 1200® series HPLC fitted with a Thermo Hypersil® Gold C18 column (15×2.1×3 µm), isocratic elution with 60/40 methanol/water (+0.1% Formic Acid), 0.4 mL/min flow rate, using a DAD detector at 285 nm. 4-(4-chlorophenyl)-5-methylene-pyrrol-2-one has a retention time of ~2.8 minutes.

The absolute level of lactam in solution is measured and reported as an increase in solubility of lactam relative to water alone. The results are shown below.

| Additive | % Additive in Water | Mean Lactam Level in Solution (ppm) | Solubility Increase vs water alone |
|---|---|---|---|
| Ethyl lactate | 0 | 5.7 | 1.00 |
| | 0.5 | 6.9 | 1.21 |
| | 1 | 6.9 | 1.21 |
| | 2 | 11.3 | 1.99 |
| | 5 | 26.4 | 4.63 |
| | 10 | 60.2 | 10.57 |

It will be appreciated that, except where expressly provided otherwise, all preferences are combinable.

The invention claimed is:

1. A composition comprising a lactam and an ethyl lactate, wherein the lactam is 4-(4-chlorophenyl)-5-methylene-pyrrol-2-one of Formula I:

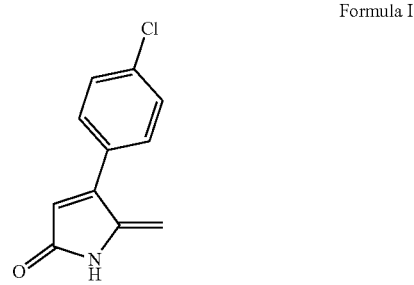

Formula I wherein the lactam is dissolved in the composition;
wherein the amount of ethyl lactate is 0.01 to 10% wt. of the composition; and
wherein the composition is at least 60 wt % water.

2. The composition of claim 1, wherein the composition is at least 70 wt % water.

3. The composition of claim 1, wherein the composition is an aqueous composition.

4. The composition of claim 1, wherein the composition is a homecare composition.

5. The composition of claim 1, wherein the composition is a personal care composition.

6. The composition of claim 1, wherein the amount of ethyl lactate is 0.01 to 5% wt. of the composition.

7. The composition of claim 1, wherein the amount of ethyl lactate is 0.01 to 3% wt. of the composition.

8. The composition of claim 1, wherein the amount of ethyl lactate is 0.01 to 1% wt. of the composition.

9. The composition of claim 1, wherein the amount of ethyl lactate is 0.001 to 1% wt. of the composition and the composition is an aqueous composition.

10. The composition of claim 1, wherein the composition comprises 0.000001 to 5% wt. lactam.

11. The composition of claim 1, wherein the composition comprises 0.001 to 5% wt. lactam.

12. The composition of claim 1, wherein the composition comprises 0.01 to 2% wt. lactam.

* * * * *